(12) United States Patent
Milstein

(10) Patent No.: US 7,138,532 B2
(45) Date of Patent: Nov. 21, 2006

(54) COLOR-STABLE, LOW IMPURITY TOCOPHEROL COMPOSITIONS AND PROCESSES FOR PREPARING THE SAME

(75) Inventor: Norman Milstein, Cincinnati, OH (US)

(73) Assignee: Cognis Corporation, Cincinnati, OH (US)

( * ) Notice: Subject to any disclaimer, the term of this patent is extended or adjusted under 35 U.S.C. 154(b) by 0 days.

(21) Appl. No.: 10/626,281

(22) Filed: Jul. 24, 2003

(65) Prior Publication Data

US 2004/0138479 A1    Jul. 15, 2004

Related U.S. Application Data

(60) Provisional application No. 60/398,900, filed on Jul. 26, 2002.

(51) Int. Cl.
*C07D 311/72*    (2006.01)

(52) U.S. Cl. .................................................. 549/408

(58) Field of Classification Search ................. 549/408
See application file for complete search history.

(56) References Cited

U.S. PATENT DOCUMENTS

| 5,670,668 A | 9/1997 | Hyatt |
| 6,414,166 B1 | 7/2002 | Lee |

OTHER PUBLICATIONS

Baxter, et al., Natural α-, β- and γ-Tocopherols and Certain Esters of Physiological Interest, JACS, vol. 65, (May 1943), pp. 918-924.

*Primary Examiner*—Taofiq Solola
(74) *Attorney, Agent, or Firm*—John F. Daniels; Arthur G. Seifert

(57) ABSTRACT

Processes for preparing color-stable, low-impurity tocopherol compositions are described, wherein the processes comprise: (a) providing a protecting group-substituted tocopherol compound, for example an acetate of a natural-source tocopherol compound; (b) purifying the protecting group-substituted tocopherol compound, for example through crystallization; and (c) solvolyzing the purified compound to form free tocopherol. Also described are the tocopherol compositions prepared thereby.

36 Claims, No Drawings

COLOR-STABLE, LOW IMPURITY TOCOPHEROL COMPOSITIONS AND PROCESSES FOR PREPARING THE SAME

CROSS-REFERENCE TO RELATED APPLICATIONS

This application claims benefit of priority, under 35 U.S.C. §119(e), of U.S. Provisional Patent Application No. 60/398,900, filed Jul. 26, 2002, the entire contents of which are herein incorporated by reference.

BACKGROUND OF THE INVENTION

As concerns over maintaining proper health continue to grow, vitamin and antioxidant use and intake also continue to rise. As more evidence of the potential benefits associated with the use and intake of vitamins and antioxidants continues to be generated, demand for such substances increases, as does the demand for purer forms thereof. Many antioxidants and vitamins can be found in, and extracted from, natural sources. However, these natural sources, e.g., plants and vegetables, contain many undesirable components and impurities which are extracted along with the antioxidants.

Additionally, the incorporation of vitamins and antioxidants into more and more varied applications has generated further challenges. For example, consumers may prefer certain aesthetic qualities which make vitamins and antioxidants that are not color stable undesirable in certain formulations.

Tocopherol compounds are components of vegetable oils which exhibit vitamin E activity. Tocopherol compounds are found widely distributed in many organic substances, including grain oils and vegetable oils. However, the amount of tocopherol present in the natural oils may be small, and therefore, the oils are distilled to concentrate the tocopherol content. Unfortunately, the content of other undesirable co-boilers, as well as pesticides, fertilizers, etc. may also be concentrated. Moreover, the products are not necessarily color-stable.

As such, there have been many attempts to recover and purify antioxidants, such as tocopherols, from natural sources. For example, a method which involves mixing a tocopherol-containing material with a polar organic solvent and contacting this mixture with a strongly basic anionic exchange resin, whereby the tocopherols are absorbed onto the resin, and subsequently eluted with an acidic solution, has been described. However, such methods can result in resin fouling, and potential oxidation of the resins may result in a persistent amine odor. Moreover, resins are short-lived, expensive and provide relatively low capacity.

Other processes for the isolation of tocopherols involve treating deodorizer distillates, which comprise the "sludge" or distillate obtained in connection with the production of edible oils and fats subsequent to the deodorization step, with a lower aliphatic alcohol in the presence of an acid catalyst, often with prior saponification of the sludge, for the purposes of esterifying the free fatty acids present in the sludge. Other processes have been disclosed wherein the tocopherols and/or sterols are esterified with the free fatty acids contained in the distillates. However, these processes are often complicated, time-consuming and expensive. Moreover, most prior art processes for the purification or isolation of tocopherols and/or sterols which involve the esterification of the tocopherols and/or sterols with free fatty acids present in the feed are incapable of adequately removing impurities and other components which co-distill with tocopherols and/or sterols, at sufficient yields.

Another process for the separation of tocopherols has been described wherein borate esters are formed, the mixture is distilled and the esters are subsequently hydrolyzed, with subsequent separation of the borate source from the tocopherol. While such a process generally removes a large portion of the impurities that co-distill with the tocopherol, significant amounts of the tocopherol in the original feed material can be lost during the purification, foaming during the esterification process is a significant problem, and undesirable borate solids can form requiring additional separation steps.

Other processes which may result in acceptable levels of certain impurities do not meet all currently desired purity specifications, and moreover, fail to provide color stability characteristics which are satisfactory in all applications.

Thus, there is a need in the art for a process by which tocopherol compounds can be purified in high yield from natural sources to provide color-stable tocopherol compositions.

BRIEF SUMMARY OF THE INVENTION

The present invention relates to processes for the purification of tocopherol compounds, wherein a high degree of purity and color-stability are obtained. The processes according to the present invention provide purified tocopherols, preferably natural tocopherols, at unexpectedly high and significantly improved yields and further remove many of the unwanted components while simultaneously providing a color-stable, aesthetically-pleasing product.

The present invention includes processes comprising: (a) providing a protecting group-substituted tocopherol compound; (b) purifying the protecting group-substituted tocopherol compound; and (c) solvolyzing the purified compound to form free tocopherol.

In accordance with preferred embodiments of the present invention, the protecting group-substituted tocopherol compound comprises an acetate of a natural-source tocopherol compound; the purification comprises crystallizing the acetate of the tocopherol compound from an isopropanol-containing solvent; and the solvolysis comprises reacting the purified acetate with an aqueous solution of sodium hydroxide in isopropanol under a nitrogen atmosphere at reflux conditions to form free tocopherol, in the presence of a reducing agent comprising sodium borohydride.

The present invention also includes processes for purifying a tocopherol compound comprising: (a) providing a starting material comprising a tocopherol compound; (b) reacting the starting material with a protecting group to form a reaction mixture comprising a protecting group-substituted tocopherol compound; (c) separating the protecting group-substituted tocopherol compound from the reaction mixture to form a purified protecting group-substituted tocopherol compound; and (d) solvolyzing the purified compound to form a free tocopherol. Additionally, the present invention includes processes comprising: (a) providing an ester of a tocopherol compound, (b) reacting the ester with an aqueous solution of a basic compound in an alcohol solvent under an inert atmosphere to form free tocopherol, in the presence of a reducing agent.

Furthermore, the present invention includes compositions comprising a natural tocopherol compound, wherein the composition has a color-stability such that the composition has a Gardner color value of less than about 6 after 24 hours at a temperature of up to about 60° C., as well as compositions comprising a color-stable, natural tocopherol compound, wherein the composition has an l-tocopherol content less than about 0.75% and a total non-α-tocopherol content of less than about 2%, preferably less than about 1.75%, more preferably less than 1.5%. The present invention includes compositions prepared in accordance with the processes of the present invention.

DETAILED DESCRIPTION OF THE INVENTION

The present invention is directed to processes for the purification of tocopherol compounds. As used herein, the term "tocopherol compounds" refers to the broad class of compounds which can be characterized as derivatives of 6-chromanol having an isoprenoid side chain, of which many are known to exhibit vitamin E activity. These compounds include, for example, the alpha (α-), beta (β-), gamma (γ-) and delta (δ-) homologues of tocopherol.

In accordance with one embodiment of the present invention, a protecting group-substituted tocopherol compound is provided. As used herein, a "protecting group" refers to a moiety capable of bonding to a tocopherol compound at the hydroxyl carbon, such that the protecting group-substituted tocopherol compound is capable of being crystallized, and the protecting group is subject to subsequent removal, i.e., lyzing from the tocopherol compound, following the crystallization. Examples of suitable protecting groups include esters, such as acetates, succinates, esters of dibasic acids, esters of unsaturated acids, phosphates, phosphinates, sulfonates and carbonates, ethers groups, and silyl groups such as trialkylsilyl halides. Preferably, the protecting group is an ester. The most preferred protecting groups are esters of monobasic carboxylic acids. Most preferably, the protecting group-substituted tocopherol compound will comprise tocopherol acetate.

In various preferred embodiments of the present invention, the tocopherol compound itself is derived from a natural source. Natural organic sources include, for example, grain oils, vegetable oils and plant sources. Examples of suitable grain and vegetable oils include wheat germ, corn, barley, rye, safflower, soybean, peanut, cottonseed, linseed, sunflower, rapeseed and palm oils. Examples of suitable plant sources from which the starting composition may be derived include palm leaves, lettuce, alfalfa, rubber latex and a variety of other plant materials. The natural sources for use in the present invention are available commercially and can also be extracted via known techniques.

Of the tocopherol compounds occurring naturally, d-α-tocopherol exhibits the most vitamin E activity. Accordingly, it is preferred that the tocopherol compound contain as much d-α-tocopherol as possible, as compared to l-stereoisomers, and β-, δ-, and γ-isomers. Preferably, the tocopherol compound will comprise at least 50% α-tocopherol based upon the total tocopherol content. More preferably, the tocopherol compound will comprise at least 70% α-tocopherol, and even more preferably, at least 80% α-tocopherol. Most preferably, tocopherol compound will comprise at least 90% α-tocopherol. In all instances, it is preferred that the tocopherol comprise a majority of the d-stereoisomer, more preferably, greater than 90% and most preferably greater than 95%.

In accordance with certain embodiments of the present invention, a protecting group-substituted tocopherol compound is provided and subsequently purified. Purification in accordance with the present invention is accomplished via non-heat intensive methods. The tocopherol compound may be purified via crystallization from an appropriate solvent, micro- and/or nano-filtration, and ion-exchange. Other non-heat intensive mechanisms which are capable of removing impurities, such as activated carbon and bleaching clay treatments, do not satisfy the color stability aspects of the present invention. Preferably, the tocopherol compound is purified via crystallization from a solvent.

In accordance with preferred embodiments of the present invention, crystallization is carried out in a solvent which comprises a lower alcohol. Lower alcohols such as methanol, ethanol, propanol, butanol, isopropanol and isobutanol are preferred. The most preferred crystallization solvent is isopropanol. Crystallization is carried out using conventional crystallization techniques, at temperatures below room temperature, and above the freezing point of the solvent. For example, when isopropanol is employed as the crystallization solvent, temperatures of from about 10° C. to about −50° C. are employed.

Once crystllization is completed, the crystallized protecting group-substituted tocopherol compound is collected, preferably via filtration. Multiple crystallization may be employed to increase purity. The collected, crystallized protecting group-substituted tocopherol compound is re-mixed, e.g., re-dissolved, in a crystallization solvent, preferably isopropanol, recrystallized and collected again. One crystallization is acceptable for purity and color-stability, depending upon feed quality and washing efficiency. Two crystallizations may be beneficial where such aspects are deficient.

The purified protecting group-substituted tocopherol compound is subsequently reacted to remove the protecting group, yielding the free tocopherol. Preferred embodiments of the present invention, wherein the protecting group comprises an ester, involve the hydrolysis of the ester group. Hydrolysis may be accomplished via acid-catalyzed reaction, or by base-promoted hydrolysis, i.e., saponification. According to preferred embodiments of the present invention, ester protecting groups are lyzed from the tocopherol compound via base-promoted hydrolysis.

Base promoted hydrolysis in accordance with more preferred embodiments of the present invention includes the reacting of the ester of the tocopherol compound with an aqueous solution of a basic compound, preferably in an alcohol solvent, also preferably at reflux conditions. The alcohol solvent is preferably isopropanol. The basic compound may include any basic compound capable of reacting with the tocopherol ester under saponification conditions. For example, alkali metal hydroxides, alkaline earth metal hydroxide, ammonium hydroxide, and metal hydrides may be used. In preferred embodiments of the present invention, alkali metal hydroxides are used. The most preferred basic compounds are sodium hydroxide and potassium hydroxide. Sodium hydroxide is most preferred for efficiency and cost.

The base-promoted hydrolysis in accordance with the present invention is preferably conducted under an inert atmosphere, preferably nitrogen. Additionally, in preferred embodiments of the present invention, the hydrolysis is carried out in the presence of a reducing agent. Suitable reducing agents include, for example, borohydrides, metal hydrides, and boranes. The most preferred reducing agent is sodium borohydride due to its mild reactivity and ease of handling.

After the protecting group-substituted tocopherol is reacted to remove the protecting group, the free tocopherol can be further purified via washing, distillation, etc.

In a preferred embodiment of the present invention, base-promoted hydrolysis, i.e., saponification, may be carried out using an esterified vegetable oil extract as the starting material for the saponification. The hydrolysis reaction may be carried out in a large (e.g., 500 gallon), multi-purpose, batch reactor. The entire saponification process in accordance with this preferred embodiment comprises charging, reacting, neutralizing, stripping, washing, stripping, and discharging, all of which can be accomplished in the batch reactor.

Initially, the esterified vegetable oil extract can be charged into the reactor along with solvent and aqueous basic solution. The water and/or solvent may be fresh or recycled from previous batches, or a mixture of both fresh and recycled streams. The reaction mixture can then be heated and held at reflux temperatures for a period of time. The hydrolyzed reaction mixture can then be cooled and acid is added to neutralize the mixture. After neutralization the isopropyl alcohol and water can be distilled off and collected for further use. The reactor contents can then be treated with heptane and washed with water to strip the vegetable oil extract and remove any water-soluble impurities.

The present invention also includes processes wherein the protecting group-substituted tocopherol is provided by reacting a tocopherol compound with a protecting group.

Compositions in accordance with the present invention include a natural tocopherol compound, wherein the composition has a color-stability such that the composition has a Gardner color value of less than about 6 after 24 hours at a temperature of up to about 60° C. Additional compound in accordance with the present invention include a color-stable, natural tocopherol compound, wherein the composition has an l-tocopherol content less than about 0.75% and a total non-α-tocopherol content of less than about 2%. Preferable impurity levels are less than about 0.65% l-tocopherol content, and more preferably less than about 0.60%. Additionally, it is preferred that the compositions in accordance with the present invention have a non-α-tocopherol content of less than about 1.75%, more preferably, less than about 1.5%, even more preferably less than about 1.0%, and even more preferably, less than about 0.8%. In the most preferred embodiments, compositions in accordance with the present invention have a non-α-tocopherol content of less than about 0.5%, based upon the total tocopherol content of the composition.

The present invention will now be illustrated in more detail by reference to the following specific, non-limiting examples.

EXAMPLE 1

Acid Catalyzed Hydrolysis of Vitamin E Acetate

The raw materials listed in Table 1 were charged into a reaction vessel in the order listed and refluxed for 4 hours at 88° C. with agitation under a nitrogen blanket, and allowed to stand under nitrogen for 48 hours.

TABLE 1

| | |
|---|---|
| Vitamin E Acetate | 50 g. |
| Isopropanol | 200 g. |
| HCl, 37% | 10.5 g. |
| Water | 43.5 g. |

Subsequently, 200 mL hot tap water and 200 mL heptane were added, and resulting layers were separated. The heptane layer was washed twice with 200 mL hot tap water to get rid of traces of HCl, and the twice washed heptane phase was dried to 110° C. with nitrogen sparge. The residue weighed 45.4 g. and was hazy, with a Gardner 1 color. Placed 17 g. of sample in the oven at 60° C. for 24 hours. The sample darkened to a Gardner 2-color.

EXAMPLE 2

Vitamin E Acetate Saponification

Using the components and amounts listed below in Table 2, the following procedure was followed. The vitamin E acetate was first charged into the reaction vessel under nitrogen. The isopropanol was then added under nitrogen with agitation. The NaOH, 40%; NaBH4, 12% were added first in 20 g. water and then the NaOH, 50% was added in a second portion of 20 g. water. The color of the reaction mixture darkened from almost colorless to light yellow upon adding the first alkaline solution. The reaction mixture was then heated to reflux for 2 hours and 15 minutes under a nitrogen blanket. The color lightened. It was then cooled to 40° C. and 14 g acetic acid were added under nitrogen with agitation. Phosphoric acid may also preferably be used in place of acetic acid. The reaction mixture was poured into a 1-liter separatory funnel, and 200 mL hot tap water and 200 mL heptane were added, shaken and the aqueous lower layer was separated off. The aqueous lower layer weighed 368 g. The heptane layer was washed three times with 200 mL hot tap water as follows:

| | |
|---|---|
| First extraction: | 265 g. lower layer out |
| Second extraction: | 226 g. lower layer out |
| Third extraction: | 206 g. lower layer out |

The heptane extract was stripped to 105° C. under a nitrogen stream. The color of the residue was ~3 on the Gardner scale. The residue was distilled at a pot temperature of 230–235° C. and 0.2 mm Hg. The distillate was almost water white. The distillate was stored under nitrogen and labeled #00099-187.

TABLE 2

| | |
|---|---|
| Vitamin E Acetate (MW = 472.7) | 100 g. |
| (Covitol ® 1360, Cognis Corp., Cincinnati, OH) | |
| Isopropanol, 99% | 200 g. |
| Water | 20 g. |
| NaOH, 40%; NaBH4, 12% | 4.17 g. |
| Water | 20 g. |
| NaOH, 50% | 15.26 g. |
| Water | 20 g. |

Subsequently, the residue was exposed to an exaggerated color stability test in which 2–3 g of #00099-187 in a 50 mL beaker was left overnight in the oven at 60° C. The sample darkened to 5 on the Gardner scale.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process for producing a color-stable, low-impurity tocopherol compound or mixture of tocopherol compounds comprising:

(a) providing a protecting group-substituted tocopherol compound;

(b) purifying the protecting group-substituted tocpharol compound by crystallizing it from a crystallization solvent and collecting the crystallized compound; and
(c) solvolyzing ibe purified compound to form free tocopherol.

2. The process according to claim 1, wherein the solvolyzing is carried out under an inert atmosphere.

3. The process according to claim 2, wherein the inert atmosphere comprises rntrogen.

4. The process according to claim 1, wherein the protecting group-substituted tocopherol compound is an ester.

5. The process according to claim 4, wherein the ester is selected from the group consisting of an acetate, a succinate, a phosphate, a phosphinate, a sulfonate and a carbonate.

6. The process according to claim 4, wherein the ester is selected from the group consisting of an acetate and a succinate.

7. The process according to claim 4, wherein the ester is an acetate.

8. The process according to claim 1, wherein the tocopherol compound comprises α-tocopherol.

9. The process according to claim 8, wherein the α-tocopherol is present in an amount of at least about 80% by weight based on the total tocopherol content.

10. The process according to claim 1, wherein the tocopherol compound comprises d-α-tocopherol.

11. The process according to claim 10, wherein the d-α-tocopherol is present in an amount of at least about 80% by weight based on the total tocopherol content.

12. The process according to claim 1, wherein the tocopherol compound is a natural-source tocopherol.

13. The process according to claim 12, wherein the protecting group-substituted tocopherol compound is an ester.

14. The process according to claim 13, wherein the ester is selected from the group consisting of an acetate and a succinate.

15. The process according to claim 13, wherein the ester is an acetate.

16. The process according to claim 1, wherein collecting the crystallized compound is by filtration.

17. The process according to claim 1, wherein the crystallization solvent comprises a lower alcohol.

18. The process according to claim 1, wherein the crystallization solvent comprises isopropanol.

19. The process according to claim 1, wherein crystallizing the compound is carried out at a temperature below room temperature and above the freezing point of the crystallization solvent.

20. The process according to claim 1, wherein the crystallization solvent comprises isopropanol and crystallizing the compound is carried out at a temperature of from about 10° C. to about -50° C.

21. The process according to claim 1, further comprising re-mixing the crystallized compound with the crystallization solvent and repeating the crystallizing and the collecting at least once in sequential order.

22. The process according to claim 1, wherein the protecting group-substituted tocopherol compound is an ester, and wherein solvolyzing the ester comprises a reaction selected from the group consisting of acid-catalyzed hydrolysis and base-promoted hydrolysis.

23. The process according to claim 1, wherein the protecting group-substituted tocopherol compound is an ester, and wherein solvolyzing the ester comprises base-promoted hydrolysis.

24. The process according to claim 23, wherein solvolyzing the ester comprises reacting the ester with an aqueous solution of a basic compound selected from the group consisting of alkali metal hydroxides, alkaline earth metal hydroxide, ammonium hydroxide, and metal hydrides.

25. The process according to claim 24, wherein the basic compound comprises an alkali metal hydroxide.

26. The process according to claim 24, wherein the basic compound comprises sodium hydroxide.

27. The process according to claim 23, wherein the hydrolysis is carried out in the presence of an alcohol solvent.

28. The process according to claim 27, wherein the alcohol solvent comprises isopropanol.

29. The process according to claim 23, wherein the hydrolysis is carried out in the presence of a reducing agent.

30. The process according to claim 29, wherein the reducing agent comprises sodium borohydride.

31. The process according to claim 15, wherein the hydrolysis is carried out under reflux conditions.

32. A process for producing a color-stable, low-impurity tocopherol compound or mixture of tocopherol compounds, said process comprising:
(a) providing an acetate of a natural-source tocopherol compound;
(b) crystallizing the acetate of the tocopherol compound from a solvent comprising isopropanol and collecting a purified acetate of the tocopherol compound; and
(c) reacting the purified acetate with an aqueous solution of sodium hydroxide in isopropanol under a nitrogen atmosphere at reflux conditions to form free tocopherol, in the presence of a reducing agent comprising sodium borohydride.

33. A process for purifying a tocopherol, said process comprising:
(a) providing a starting material comprising a tocopherol compound;
(b) reacting the starting material with a protecting group to form a reaction mixture comprising a protecting group-substituted tocopherol compound;
(c) separating the protecting group-substituted tocopherol compound from the reaction mixture to form a purified protecting group-substituted tocopherol compound; and
(d) solvolyzing the purified compound in the presence of a reducing agent to form a free tocopherol.

34. A process for purifying a tocopherol, said process comprising:
(a) providing an ester of a tocopherol compound,
(b) reacting the ester with an aqueous solution of a basic compound in an alcohol solvent under an inert atmosphere to form free tocopherol, in the presence of a reducing agent.

35. A composition comprising a natural tocopherol compound, wherein the composition has a color-stability such that the composition has a Gardner color value of less than about 6 after 24 hours at a temperature of up to about 60° C.

36. A composition comprising a color-stable, natural tocopherol compound, wherein the composition has an l-tocopherol content less than about 0.75% and a total non-α- tocopherol content of less than about 2%.

* * * * *